United States Patent [19]

Liang et al.

[11] Patent Number: 5,495,177

[45] Date of Patent: Feb. 27, 1996

[54] METHOD AND APPARATUS FOR DIELECTRIC SENSING IN A THERMOPLASTIC WINDING PROCESS

[75] Inventors: Steven Y. Liang, Marietta; Joseph A. Urquhart-Foster, Atlanta, both of Ga.

[73] Assignee: Georgia Tech Research Corporation, Atlanta, Ga.

[21] Appl. No.: 364,516

[22] Filed: Dec. 27, 1994

Related U.S. Application Data

[63] Continuation of Ser. No. 1,499, Jan. 7, 1993, abandoned.

[51] Int. Cl.⁶ ................................................. G01R 27/26
[52] U.S. Cl. ........................................... 324/663; 324/690
[58] Field of Search ..................... 324/658, 663, 324/671, 679, 686, 690

[56] References Cited

U.S. PATENT DOCUMENTS

| | | | |
|---|---|---|---|
| 3,730,086 | 5/1973 | Dautermann | 324/684 |
| 3,950,698 | 4/1976 | Wochnowski | 324/687 |
| 4,399,100 | 8/1983 | Zsolnay et al. | 364/500 |
| 4,546,645 | 10/1985 | Delmulle et al. | 324/690 |
| 4,723,908 | 2/1988 | Kranbuehl | 324/687 |
| 5,119,022 | 6/1992 | Kranbuehl et al. | 324/236 |
| 5,177,446 | 1/1993 | Boriani et al. | 324/671 |

FOREIGN PATENT DOCUMENTS

| | | | |
|---|---|---|---|
| 491023 | 9/1972 | U.S.S.R. | 324/690 |

OTHER PUBLICATIONS

Ciriscioli, P. R. and Springer, G. S., "Dielectric Cure Monitoring—A Critical Review", *SAMPE Journal*, vol. 25, No. 3, May/Jun. 1989, pp. 35–42.

Wilson, Brian A., "Filament Winding . . . Past, Present, and Future", *Proceedings of the 34th International SAMPE Symposium*, May 1989, pp. 2429–2439.

Egerton, M. W. and Gruber, M. B., "Thermoplastic Filament Winding Demonstrating Economics and Properties Via In–Situ Consolidation", *Proceedings of the 33rd International SAMPE Symposium*, Mar. 1988, pp. 35–47.

Kranbuehl, D. E., Delos, S. E., Yi, E. C. and Mayer, J. T., "Dynamic Dielectric Analysis: A Nondestructive Cure Process Monitoring Method", *Review of Progress in Quantitative Nondestructive Evaluation*, vol. 5B, 1986, pp. 1030–1038. (month unavailable).

*Primary Examiner*—Kenneth A. Wieder
*Assistant Examiner*—Christopher M. Tobin
*Attorney, Agent, or Firm*—Needle & Rosenberg

[57] ABSTRACT

Disclosed are a method and apparatus for real time process monitoring of thermoplastic filament winding. During processing, the thermoplastic filament winding is wound around an electrically conductive mandrel. An electrically conductive roller, juxtaposed and movable radially with respect to the mandrel, is provided for compression of the portion of the thermoplastic filament disposed on the mandrel. Accordingly, a dielectric capacitor is formed between the mandrel and the roller with the portion of the thermoplastic disposed between the mandrel and roller acting as the dielectric of the capacitor. An input voltage is applied to the dielectric capacitor, and the permittivity and loss factor of the capacitor are determined by monitoring the input voltage and output current to thereby determine the degree to which the thermoplastic has consolidated.

4 Claims, 1 Drawing Sheet

METHOD AND APPARATUS FOR DIELECTRIC SENSING IN A THERMOPLASTIC WINDING PROCESS

This application is a continuation, of application Ser. No. 08/001,499, filed Jan. 7, 1993, now abandoned.

BACKGROUND OF THE INVENTION

1. Field of the Invention

This invention relates to dynamic dielectric analysis as a sensing methodology applied to real-time process monitoring for thermoplastic filament winding.

2. Background Art

Filament winding is a process where fibers are placed on a rotating mandrel in a predetermined path to form a given shape or part. By combining the fibers with a resin binder, a finished part with desirable mechanical properties results. Filament winding is primarily used to form products such as pipes, vessels, or tanks which are subject to internal pressure. Other applications, such as high strength, low weight control rods or other slender structural elements subject to torsion, are commonly filament wound.

Current filament winding techniques frequently use thermosetting resins which require post-curing procedures in an autoclave or oven. The advent of high strength thermoplastic resins has allowed the process to be completed at the time of winding since temperature and pressure can be applied simultaneously during the winding process. This process is called "in-situ" consolidation of the resin and fiber. Thermoplastic tape pre-impregnated with reinforcing fibers (prepreg tape) along its length is the usual product form used as input for an in-situ consolidation winding process.

An ability to consolidate the finished product during the winding process offers the advantage of eliminating the need for post-curing or autoclaving. The removal of autoclaving from the process provides strong economic incentives to apply in-situ consolidation to as many processes as possible. Additional advantages of the in-situ consolidation process over the traditional thermoset filament winding include the ability of making wound parts with low winding angles and thin cross sections.

Even with the above mentioned advantages, in-situ consolidation has yet to be widely accepted by the industry because current in-situ consolidated parts tend to have a higher void content than autoclaved parts. Void content refers to the number and volume of trapped air bubbles or other foreign objects in the resin of the finished product. Void content is normally referred to as a percentage of the overall volume of the part. Autoclaved parts can have void contents as low as 1% while in-situ consolidated parts fall in the range of 5–10%.

Current void content measurement for filament wound parts are completed off-line by ultrasonic attenuation, X-radiography, Fokker bond testing, optical holographic stress wave interferometry or thermography. However, none of these methods of measurement is currently applied in real time nor would they be suitable for application to a control process. This lack of suitability results from difficulties in implementation into current winding equipment, the speed at which measurements are made, or possible structural damage to the part itself.

Therefore, it is desirable to provide real-time monitoring of thermoplastic filament winding to ensure proper in-situ consolidation, especially considering the strong economic advantages. Industrial applications of thermoplastic filament winding with in-situ consolidation have been limited thus far by the void content of wound parts resulting from the variation of resin consolidation at the filament lay down point.

SUMMARY OF THE INVENTION

The present invention provides a method and apparatus for real-time process monitoring of thermoplastic filament wound composites by means of dielectric monitoring. This invention includes the utilization of a sinusoidal input current passing through the contact point of the thermoplastic tape on the filament winder. Temperature and pressure induce dielectric changes in the polymer at the lay down point which will change the magnitude and phase of the current passing through that point. Relating the electrical current parameters back to the dielectric quantities, plus accounting for the process variables, allows real-time monitoring of the procedure.

The dielectric monitoring is accomplished by an electrical circuit that contains resistive and capacitive elements, as well as amplifiers and an input signal source. The primary element of interest is the capacitor that is formed by the thermoplastic tape as its dielectric with the mandrel around which the thermoplastic tape is wound and the pressure roller at the laydown point acting as the "plates" of the capacitor.

This real-time monitoring of the thermoplastic filament windings presents many technological advantages. This control gained through monitoring will enable the process to produce higher quality parts on a larger scale and in a wider array of applications than current uses permit. In particular, application of the process to automotive products is one of the possible benefits for implementation of the real-time process control.

Without an effective monitoring methodology, excessive amounts of heat and pressure are commonly applied during the filament winding process. Although the objective of heat and pressure is to reduce the void content, too much of either parameter causes problems in the finished product. Overpressurization causes an unusually high fiber volume fraction by squeezing too much resin away from the fibers. Too much heat can degrade the thermoplastic matrix and adversely effect the mechanical properties of the finished product.

Compared to other technologies, advantages of the dielectric methodology include real-time sensing, ease of attachment to the filament winding machine, and sensitivity to process parameter changes.

DETAILED DESCRIPTION OF THE INVENTION

The present invention may be understood more readily by reference to the following detailed description of specific embodiments and the Example and Figures included therein.

As used in the claims, "a" means one or more.

The preferred embodiments of the present invention are now described with reference to the drawings, in which like numbers indicate like parts throughout the views.

In order to provide real-time monitoring of the thermoplastic filament winding, an electric circuit is formed across the components. Sinusoidal electric excitation is applied across electrodes to establish a time-varying electrical field. The resulting current waveform is compared to the input voltage input signals, which allows real-time process monitoring.

Figure 1:
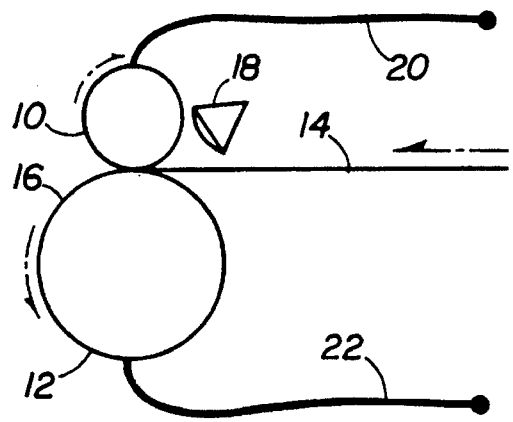
FIG. 1 is a schematic illustration of an embodiment of an in-situ monitoring device of the present invention.

FIG. 1 shows the pressure roller 10 and mandrel 12 that sandwich a thermoplastic tape 14 being wound around the surface of the mandrel 12 to form a layer of plastic 16. Heat source 18 provides the heat necessary to raise the temperature of the thermoplastic tape or resin above its melting point.

The roller 10 and mandrel 12 are comprised of electrically conducting material and the plastic material between the mandrel and roller acts as a dielectric to form a capacitor when an electric potential is applied from a power supply connected to the roller 10 by conductor 20 and the mandrel 12 by conductor 22. Although the geometry is clearly different than for a parallel plate capacitor, the capacitance rating of such a roller/thermoplastic combination remains proportional to the permittivity of the dielectric material between the conductors. The permittivity of thermoplastics will vary during the temperature and pressure cycle of manufacturing processing. Thus, the pressure roller/thermoplastic tape/mandrel combination represents a varying capacitor as the tape undergoes the temperature and pressure cycles of processing on the filament winder.

Figure 2:
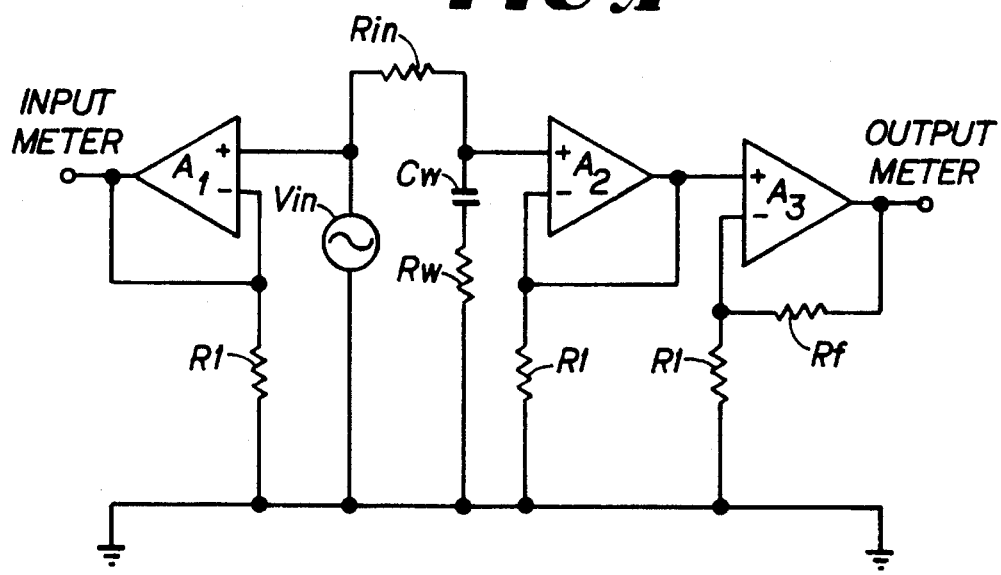
FIG. 2 is a schematic drawing of a monitoring circuit for dynamic dielectric monitoring of the thermoplastic filament winding.

FIG. 2 is an electric circuit for monitoring the characteristics of the winding. The electrical characteristics of the device of FIG. 1 are represented as varying capacitor $C_w$, the winding machine capacitance. Also, a small resistance exists between the varying capacitor and ground, represented as $R_w$. It has been found that $C_w$ may have a magnitude of about 10 pF and $R_w$ may be between 3 and 10 ohms. This circuit model is incorporated into a sensing circuit design which includes elements associated with the measurement of sensor input and output quantities. A series input resistor $R_{in}$ provides a voltage divider for the output. By choosing a larger input resistance, such as 1 megaohm, resistor $R_{in}$ also masks small changes in the modeled resistance to ground, such as the changes resulting from the temperature variations of components. A typical value for resistor $R_1$ is 1 megaohm. The time-varying input voltage source is shown in FIG. 2 as $V_{in}$, typically 5 volts (peak-to-peak). This circuit applied to the sensor design of FIG. 1 was found to be most sensitive at an input frequency of around 13 kHz.

To monitor the varying capacitor, the following circuit parameters may be compared: input voltage, output voltage, current and phase of the circuit. These parameters are monitored at the input meter and output meter connections shown in FIG. 2. The meters, by design, have a relatively high impedance. However, the similarly high value of $R_{in}$ may cause the circuit element impedances to be on the same order of magnitude. Since the circuit and meter capacitances are in parallel, they are additive. Therefore, circuit buffers are added in the form of operational amplifiers in a voltage follower mode to reduce the loading effects of the meters and increase the impedance by orders of magnitude. This resulting increased complex impedance causes the capacitance presented to the system to drop. As shown in FIG. 2, two operational amplifiers $A_1$, $A_2$ serve to buffer the input and output meters. A third operational amplifier $A_3$ is included to amplify the output signal.

Figure 3:
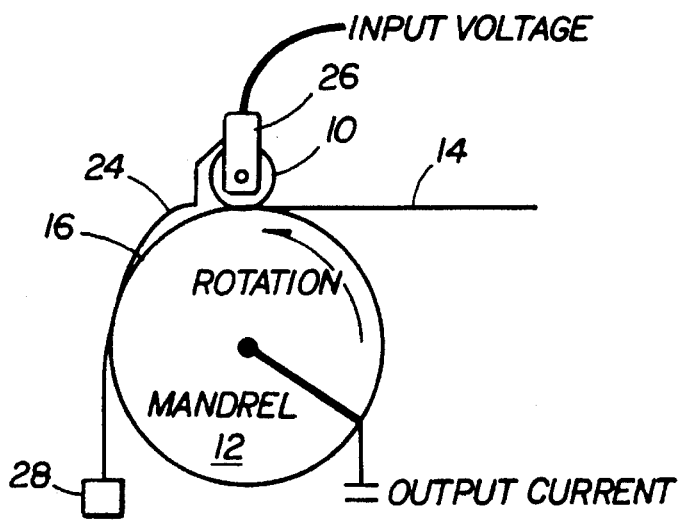
FIG. 3 is a schematic illustration of an embodiment of the present invention comprising a copper capacitance enhancement.

In addition to increasing the sensitivity of the monitoring circuit to the winder capacitance, a method of increasing the capacitance $C_w$ of the winder itself is beneficial. An additional conduction path may be created from the input through the polymer tape to the mandrel, as shown in FIG. 3. The additional conduction path for the sensor input is made by placing a narrow copper strip 24 between a conductive mounting bracket 26 for pressure roller 10 and the outer surface of the composite ring 16 on the mandrel 12. This copper strip 24 is the width of the plastic tape 14, and it is held against the composite ring 16 via a weight 28 which pulls the copper strip taut against the mandrel 12. The modification increases the percentage of overall capacitance held by the winder as well as increasing the magnitude of the winder capacitance itself.

It has been found that the monitoring circuit of FIG. 2 when applied to the sensor design of FIG. 3 is most sensitive at an input frequency of about 35 kHz.

EXAMPLE

The filament winding station used for this example was a two-axis McClean-Anderson model W-1. The machine itself consisted of an electric motor connected with a variable hydraulic transmission to control winding speed, an adjustable mandrel bed, and a mechanically driven carriage with crosshead speed adjustment. The mandrel was 178 mm in diameter and 305 mm in length, and was fabricated out of aluminum.

The in-situ consolidation mechanism was mounted to a swing arm on the crosshead and all parts of it, therefore, maintain a consistent orientation to the prepreg tape being laid down on the mandrel. The consolidation pressure mechanism consisted of a pressure roller to compact the incoming tape onto the substrate. Two rollers were used in the example, one with a width of 9.5 mm wide and a diameter of 29 mm, the other had a width of 12.7 mm and a diameter of 43.2 mm. Designed to bear the high heat of processing temperatures for advanced thermoplastics, the roller bearing was of a fully-complimented design and was cooled by pressurized air during the winding process. PEEK (Poly (etheretheretone))/glass prepreg tape was utilized, specifically, ICI Fiberite APC-2-52 Glass prepreg tape in 6.1 mm width and 0.2286 mm thickness.

Heat was applied to the laydown area via two electrical resistance hot air guns supplied by regulated air and open loop voltage controllers. The air guns, one to heat the preprocessed layers of tape and mandrel, the other to heat the incoming prepreg tape, were Convectronics, Inc. model 001s with ratings of 2000 watts and 4000 watts, respectively, at 240 volts. The temperature that these heat guns produce in their exit air steams was monitored real-time via a data acquisition board connected to a computer that utilized Workbench I/O software V.3.0.3 by Strawberry Tree, Inc.

The dielectric monitoring system itself was comprised of four primary parts. The sinusoidal input signal to be used by the circuit was generated by a Tektronix model FG 502 function generator. The sinusoidal input signal was carried to the monitoring circuit via a Pompano, Inc., BNC coaxial cable.

The monitoring circuit itself was created on an AP Products ACE 109 electronic circuit prototype board. The circuit elements themselves were carbon film resistors, one. Texas Instruments MC 1458 dual operational amplifier 8 pin DIP integrated circuit for oscilloscope channel buffering and one Texas Instruments CA 741CE operational amplifier 8 pin DIP integrated circuit to amplify the dielectric sensor output signal. Once the signal crossed the input resistor, $R_{in}$, it was carried to the winder capacitance by an alligator clamp connection cable which was mounted between the $R_{in}$ resistor and the compression roller support arm on the winding machine. This support arm was isolated electrically from the rest of the machine by an acrylic mounting block. The operational amplifiers require a supply signal which was supplied in both −15 and +15 volt form via a Tektronix PS 503A dual power supply.

The output signal as well as the input signal were fed into Pomona, Inc., BNC cables with alligator clip attachments. These cables connected to a Tektronix 2232 digital storage oscilloscope with a 100 MHz sampling capability. This oscilloscope's digital storage modes allowed for passive signal processing of the sensor output signal via a signal averaging function which averaged the signal with a 20 MHz frequency, or every five samples at the 100 MHz sampling rate. The results are summarized in the table below:

| Test | Variation | Result |
| --- | --- | --- |
| Heat Flux | Turned Off Heat | Small drop in permittivity |
|  |  | No change in loss factor |
| Winding Speed (large roller) | 33% increase in speed | 16% increase in permittivity No change in loss factor |
| Winding Speed (small roller) | 33% increase speed | No change in permittivity 10% decrease in loss factor |
| Winding Pressure | 33% increase in pressure | 10% increase in permittivity No change in loss factor |
| Local Sensitivity | Insert Alluminum Foil | 36% magnitude drop 15% phase shift |

The sensor was mildly sensitive to the different winding speeds (the second 33% faster than the first) used to produce two otherwise similar rings. In this example, using the smaller roller the permittivity showed no significant change, but the loss factor at the higher winding speed had a 10% lower steady state value. When the set-up was changed by the increase in diameter of the pressure roller, however, the permittivity showed the most sensitivity (an increase of 16%) to winding speed changes while the loss factor changed little. These contradictory results demonstrate that the sensor output is a complex interrelationship between the equipment set-up. Thus, dielectric trends between one set-up may not necessarily be extrapolated to other set-ups.

Other improvements in the circuit are also within the scope of this invention. The capacitance value of the apparatus may be increased, and the circuit can be redesigned to achieve higher levels of sensitivity to the change in that capacitance. Also, a monitoring circuit with heightened sensitivity to capacitance changes combined with a roller/mandrel combination with increased capacitance will allow a greater range of input frequencies.

What is claimed is:

1. A thermoplastic filament winding apparatus for consolidating thermoplastic filament using heating and compression of the filament, comprising:

a. an electrically conductive mandrel around which the thermoplastic filament is wound;

b. means to apply heat to the portion of the filament being wound;

c. an electrically conductive roller, juxtaposed with said mandrel and movable radially with respect to said mandrel, to provide for compression of the portion of such thermoplastic filament being wound onto said mandrel, said portion of the thermoplastic filament disposed on said mandrel and said roller disposed on said portion of the thermoplastic filament, such that a dielectric capacitor having two conductive surfaces and a dielectric material disposed therebetween is formed, with said roller and said mandrel comprising the conductive surfaces of the capacitor and the portion of the thermoplastic filament disposed between said roller and said mandrel comprising the dielectric material of the capacitor, the thickness of the dielectric material varying as the filament is wound;

d. electronic signal generating means for generating a sinusoidal electric signal to be introduced to said mandrel and said roller, said electric signal comprising an input voltage applied across the dielectric capacitor formed between said mandrel and said roller; and e. electronic monitoring means for continuously measuring said input voltage and an output current, and for determining the permittivity and the loss factor from the measured input voltage and the measured output current of the dielectric capacitor formed by mandrel, roller and thermoplastic filament as the filament is wound onto said mandrel.

2. The apparatus of claim 1 wherein said electronic monitoring means determines the permittivity and the loss factor of the dielectric capacitor formed by said mandrel, roller and thermoplastic filament by monitoring:

a. the input voltage applied to the conductive surfaces of the capacitor;

c. the output current measured from the conductive surfaces of the capacitor; and d. the phase difference between the input voltage and the output current.

3. The apparatus of claim 1 further comprising an electrically conductive strip in electrical connection with said roller, such strip extending from said roller and in contact with the thermoplastic filament on said mandrel at a point circumferentially away from the point where said roller is in contact with the thermoplastic filament.

4. A method for real time monitoring of thermoplastic filament winding, comprising:

a. winding the thermoplastic filament onto a mandrel having an electrically conductive circumferential surface;

b. applying an adjustable pressure, by a roller having an electrically conductive surface, to the thermoplastic filament as it is being wound onto said mandrel, such that said roller moves radially away from said mandrel as the thickness of the wound filament increases;

c. applying heat to the thermoplastic filament;

d. introducing an electrical signal, having an input voltage, said input voltage supplied across the electrically conductive surfaces of said mandrel and said roller, such that said mandrel, roller and the thermoplastic material located therebetween form a dielectric capacitor, with said mandrel and said roller acting as the conductive surfaces of the capacitor and the portion of the thermoplastic disposed between said mandrel and said roller acting as the dielectric of the capacitor, having an output current when said electrical signal is introduced to said conductive surfaces of said capacitor; and e. monitoring the permittivity and the loss factor of the dielectric capacitor formed by said mandrel, roller and thermoplastic material as the thermoplastic filament is wound onto said mandrel by measuring the magnitudes of the input voltage and the output current and determining the phase difference between the input voltage and the output current, to determine the degree to which the thermoplastic has consolidated.

* * * * *